US00PP14015P29

(12) United States Plant Patent
Heims

(10) Patent No.: US PP14,015 P2
(45) Date of Patent: Jul. 22, 2003

(54) PULMONARIA PLANT NAMED 'IRISH SPRING'

(75) Inventor: Daniel M. Heims, Portland, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 10/172,460

(22) Filed: Jun. 12, 2002

(51) Int. Cl.[7] ..... A01H 5/00
(52) U.S. Cl. ..... Plt./263
(58) Field of Search ..... Plt./263

*Primary Examiner*—Bruce R. Campell
*Assistant Examiner*—A Para
(74) *Attorney, Agent, or Firm*—Klarquist Sparkman, LLP

(57) ABSTRACT

A new and distinct cultivar of Pulmonaria plant characterized by lime green blotches and spots over contrasting deep green foliage and purple pink flowers changing to deep violet blue, and with mildew resistance.

2 Drawing Sheets

Botanical classification: Pulmonaria hybrid.
Variety denomination: 'Irish Spring'.

BACKGROUND OF THE INVENTION

The present invention relates to a new and distinct cultivar of a hardy perennial of the genus Pulmonaria, and known by the cultivar name 'Irish Spring'. The genus Pulmonaria is a member of the family Boraginaceae.

The new cultivar originated as an open-pollinated cross between unknown parents in a field of selected hybrid Pulmonaria. This is known to be an outcross because Pulmonaria does not normally self-pollinate. Due to the fact that the instant plant and parent plants are interspecific hybrids from several generations of interbreeding and selecting, no species designations are given.

This plant is characterized by the following:

1. Deep green foliage with a lime green overlay to the margin or blotched on the surface.
2. Deep pink flowers changing to deep violet blue.
3. Mildew resistance.

This new cultivar has been reproduced only by asexual propagation (division and tissue culture). Each of the progeny exhibits identical characteristics to the original plant. Asexual propagation by tissue culture using standard micropropagation techniques with terminal and lateral shoots as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

DETAILED PLANT DESCRIPTION

Figure 1:
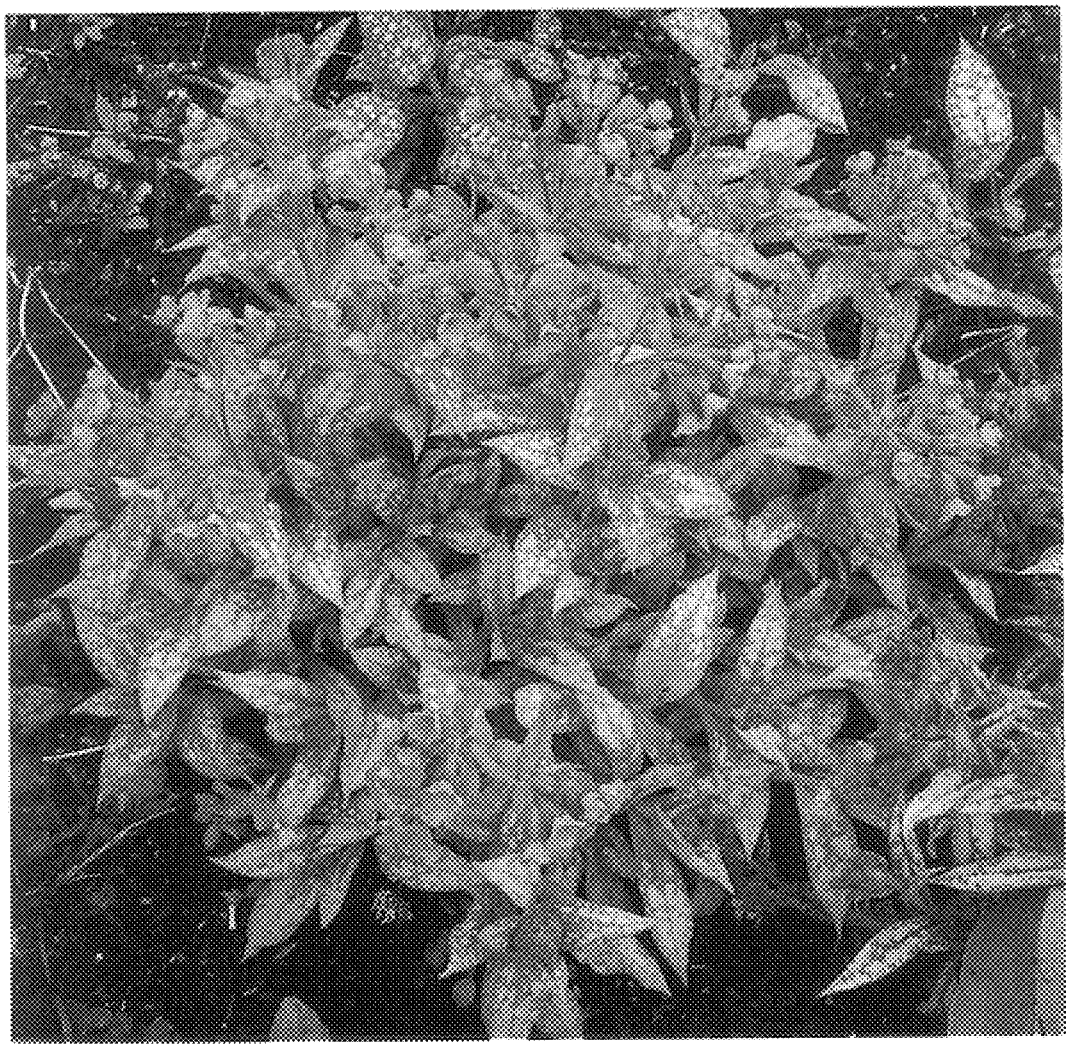
FIG. 1 shows a two-year-old Pulmonaria 'Irish Spring' in the garden in flower in April.
Figure 2:
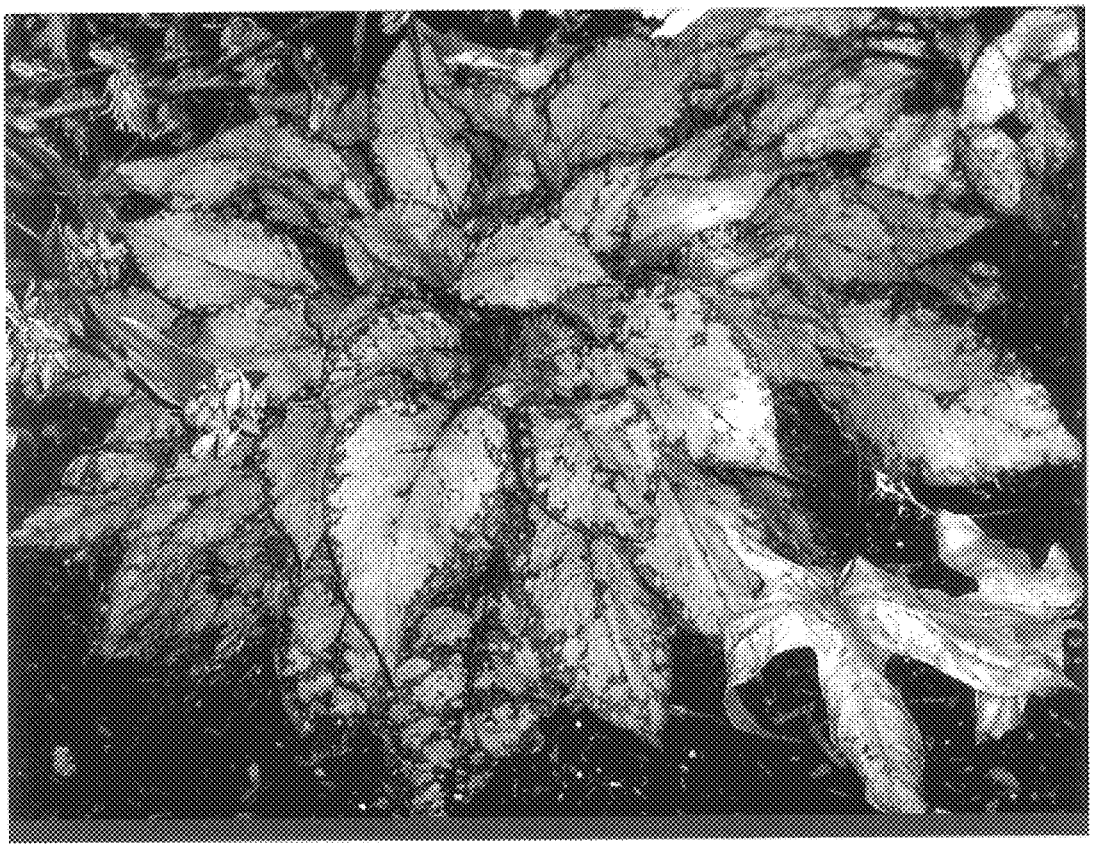
FIG. 2 shows the foliage of the same plant in the garden in July in Canby, Oreg.

The following is a detailed description of the new Pulmonaria hybrid based on observations of a two-year old specimen grown in the garden in Canby, Oreg. The color descriptions are all based on The Royal Horticultural Society Colour Chart.

Botanical name: Pulmonaria hybrid.
Cultivar name: 'Irish Spring'.
Plant:
- *Type.*—Herbaceous perennial.
- *Hardiness.*—USDA Zones 5 to 9.
- *Size.*—53 cm. wide and 30 cm. tall.
- *Form.*—Basal clump, low growing.

Leaf:
- *Type.*—Simple.
- *Shape.*—Ovate to elliptic.
- *Arrangement.*—Rosette.
- *Length.*—Ranges from 28 to 33 cm. long including petiole.
- *Width.*—8.5 cm. at widest.
- *Petiole size.*—10 cm. long, 9 mm wide.
- *Margins.*—Entire, undulating, and hirsute.
- *Apex.*—Acuminate.
- *Base.*—Attenuate.
- *Leaf and petiole texture.*—Hirsute.
- *Petiole color.*—Yellow Green 146B with margins Green 137A.
- *Venation.*—Pinnate.
- *Color.*—Topside — Deep green covered to margins or blotched with lime green. The deep green between the blotches and on the edges is Green 137A and Green 139A. The lime green "silvering" or blotches is a color not in The R.H.S. chart between their Greyed Green 193B and Yellow Green 148B. Bottom — Yellow Green 146C.

Cauline leaves (found in the spring only on the flowering stems):
- *Type.*—Simple.
- *Arrangement.*—Alternate.
- *Shape.*—Oblanceolate to ovate.
- *Length.*—8 cm.
- *Width.*—2.5 cm.
- *Margins.*—Undulate and ciliate.
- *Apex.*—Acuminate.
- *Base.*—Clasping, sessile.
- *Leaf texture.*—Hirsute.
- *Venation.*—Pinnate.

*Color.*—Topside: Ranging from Yellow Green 146A to B with spots or blotches of silvering, closest to Greyed Green 193A. Bottom side: Yellow Green 148D.

Inflorescence:

*Type.*—Terminal forked cyme.

*Peduncle.*—Height: 14 cm. Diameter: 0.4 cm. Color: Yellow Green 144A. Texture: Scabrous.

*Pedicel.*—Length: Varies. Grows to 1.4 cm. Texture: Scabrous. Color: Brown 200B.

Flower bud:

*Size.*—1.6 cm. long and 0.4 cm. wide.

*Shape.*—Ovoid on a tube, with 0.55 cm of corolla showing.

*Color.*—Red. Red Group 51A with darker areas of Red Purple 63A.

Flower:

*Type.*—Actinomorphic.

*Shape.*—Funnelform.

*Size.*—2 cm. deep and 2 cm. wide.

*Corolla.*—5 fused petals with rounded lobes.

*Color.*—Changes with maturity. Newly opened flowers are light rose red, Red 51B. They change to blue rose, Red Purple 63C with a Violet Blue 90A overlay on the lobes. Mature flowers are a deep violet blue, Violet Blue 94A.

*Calyx.*—5 fused sepals, tubular campanulate, lobes parted ¼ to base, scabrous. Color — Yellow Green 146A, brownish on the lobe edges, Brown 200C. Size — 1.7 cm deep and 0.8 cm wide.

*Pistil.*—1.6 cm. long, pin type, exerted from corolla tube.

*Ovary position.*—Partly inferior.

*Carpel number.*—4.

*Stamen number.*—5, attached to the tube.

*Pollen color.*—White 155A.

*Bloom period.*—April to May in Canby, Oreg.

*Fragrance.*—None.

Seed:

*Type.*—4 smooth nutlets, Black 202A and shiny, typical of the genus.

*Fertility.*—Fertile.

Disease: Mildew resistant, the main problem for Pulmonaria. No mildew observed on plants grown under commercial conditions in Canby, Oreg.

COMPARISONS TO SIMILAR PULMONARIA

Compared to Pulmonaria 'Emerald Isles' (U.S. Plant Pat. No. 12,339), the instant plant also has light green spots and blotches, but Pulmonaria 'Irish Spring' has lighter spots and blotches and a lower, flatter habit of growth. The new cultivar also has larger flowers with a darker blue violet color. The cauline leaves of Pulmonaria 'Emerald Isles' are rounder and shorter.

I claim:

1. A new and distinct cultivar of Pulmonaria plant as shown and described.

* * * * *